(12) United States Patent
Rorrer et al.

(10) Patent No.: US 10,793,506 B2
(45) Date of Patent: Oct. 6, 2020

(54) CONVERSION OF DICARBOXYLIC ACIDS TO MONOMERS AND PLASTICIZERS

(71) Applicant: Alliance for Sustainable Energy, LLC, Golden, CO (US)

(72) Inventors: Nicholas Rorrer, Golden, CO (US); Gregg Tyler Beckham, Golden, CO (US); Caroline Bradshaw Hoyt, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/789,794

(22) Filed: Feb. 13, 2020

(65) Prior Publication Data

US 2020/0255368 A1 Aug. 13, 2020

Related U.S. Application Data

(60) Provisional application No. 62/805,042, filed on Feb. 13, 2019.

(51) Int. Cl.
*C07C 69/44* (2006.01)
*C07C 69/602* (2006.01)
*C08L 77/00* (2006.01)

(52) U.S. Cl.
CPC .......... *C07C 69/44* (2013.01); *C07C 69/602* (2013.01); *C08L 77/00* (2013.01)

(58) Field of Classification Search
CPC ........ C07C 69/44; C07C 69/602; C08L 77/00
See application file for complete search history.

(56) References Cited

U.S. PATENT DOCUMENTS

| | | | | |
|---|---|---|---|---|
| 3,497,479 | A | * | 2/1970 | Cassar ............... C08G 69/26 528/339 |
| 4,310,638 | A | * | 1/1982 | Coran ................ C08L 23/0869 524/514 |
| 9,073,867 | B2 | * | 7/2015 | Coudray ............. C07C 209/48 |
| 2017/0130001 | A1 | | 5/2017 | Hernandez et al. |

FOREIGN PATENT DOCUMENTS

JP 2010-254932 A 11/2010

OTHER PUBLICATIONS

Dobslaw et al., "Degradation of toluene by ortho cleavage enzymes in Burkholderia fungorum FLU100", Microbial Biotechnology, 2014, vol. 8, pp. 143-154.

Xiong et al. "Scalable production of mechanically tunable block polymers from sugar", Proceedings of the National Academy of Sciences of the United States of America, Jun. 2014, vol. 111, No. 23, pp. 8357-8362.

* cited by examiner

*Primary Examiner* — Paul A Zucker
(74) *Attorney, Agent, or Firm* — Michael A. McIntyre (57) ABSTRACT

The present disclosure relates to a composition that includes a first repeat unit defined by

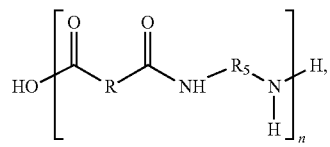

where R includes a first hydrocarbon chain that includes at least one olefinic bond, $R_5$ includes a second hydrocarbon chain, the second hydrocarbon chain may be saturated, and n may be between 2 and 1,000.

3 Claims, 5 Drawing Sheets

CONVERSION OF DICARBOXYLIC ACIDS TO MONOMERS AND PLASTICIZERS

CROSS-REFERENCE TO RELATED APPLICATIONS

This application claims priority from U.S. Provisional Patent Application No. 62/805,042 filed Feb. 13, 2019, the disclosure of which is incorporated herein by reference in its entirety.

CONTRACTUAL ORIGIN

This invention was made with government support under Contract No. DE-AC36-08GO28308 awarded by the Department of Energy. The government has certain rights in the invention.

SUMMARY

An aspect of the present disclosure is a composition that includes a first repeat unit defined by where R includes a first hydrocarbon chain that includes at least one olefinic bond, $R_5$ includes a second hydrocarbon chain, the second hydrocarbon chain may be saturated, and n may be between 2 and 1,000. In some embodiments of the present disclosure, the first hydrocarbon chain may be between 3 and 10 carbon atoms. In some embodiments of the present disclosure, the first hydrocarbon chain may further include at least one alkyl group. In some embodiments of the present disclosure, the alkyl group may include at least one of a methyl group, an ethyl group, a propyl group, and/or a butyl group.

In some embodiments of the present disclosure, the composition may further include a second repeat unit defined by, where R* includes a third hydrocarbon chain that may be saturated or unsaturated, $R_5$* includes a fourth hydrocarbon chain, the fourth hydrocarbon chain may be saturated, and m may be between 2 and 1,000.

In some embodiments of the present disclosure, the composition may further include a third repeat unit defined by, where R includes a fifth hydrocarbon chain that may be saturated or unsaturated, $R_5$ includes a sixth hydrocarbon chain, the sixth hydrocarbon chain may be saturated, and o may be between 2 and 1,000.

In some embodiments of the present disclosure, the composition may be

An aspect of the present disclosure is a composition that includes a first repeat unit defined by where $R_3$ includes a first hydrocarbon chain comprising at least one sulfur containing functional group, $R_5$ includes a second hydrocarbon chain, the second hydrocarbon chain may be saturated, and n may be between 2 and 1,000. In some embodiments of the present disclosure, the first hydrocarbon chain may include between 3 and 10 carbon atoms. In some embodiments of the present disclosure, the first hydrocarbon chain may further include at least one alkyl group. In some embodiments of the present disclosure, the alkyl group may include at least one of a methyl group, an ethyl group, a propyl group, and/or a butyl group.

In some embodiments of the present disclosure, the composition may include

In some embodiments of the present disclosure, the composition may further include a second repeat unit defined b where $R_3^*$ includes a third hydrocarbon chain that may or may not include at least one sulfur containing functional group, $R_5^*$ includes a fourth hydrocarbon chain, the fourth hydrocarbon chain may be saturated, and m may be between 2 and 1,000.

In some embodiments of the present disclosure, the composition may further include a third repeat unit defined b where $R_3^{}$ includes a fifth hydrocarbon chain that may or may not include at least one sulfur containing functional group, $R_5^{}$ includes a sixth hydrocarbon chain, the sixth hydrocarbon chain may be saturated, and o may be between 2 and 1,000.

An aspect of the present disclosure is a composition that includes where R includes a first hydrocarbon chain, $R^1$ includes a second hydrocarbon chain, and $R^2$ includes a third hydrocarbon chain. In some embodiments of the present disclosure, at least one of R, $R^1$, and/or $R^2$ may be saturated. In some embodiments of the present disclosure, at least one of R, $R^1$, and/or $R^2$ may be unsaturated. In some embodiments of the present disclosure, at least one of R, $R^1$, and/or $R^2$ may be a straight chain having between 3 and 10 carbon atoms.

In some embodiments of the present disclosure, the composition may have the structure In some embodiments of the present disclosure, the composition may have the structure

BRIEF DESCRIPTION OF THE DRAWINGS

Some embodiments are illustrated in referenced figures of the drawings. It is intended that the embodiments and figures disclosed herein are to be considered illustrative rather than limiting.

DETAILED DESCRIPTION

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to unsaturated dicarboxylic acids, for example muconic acid and/or a alkylated muconic acid, produced from the conversion of aromatic compounds such as phenols and/or cresols, and the conversion of these unsaturated dicarboxylic acids to useful polymers and/or polymer additives. As shown herein, alkylated unsaturated dicarboxylic acids, e.g. methylated muconic acid, can act as a more efficient plasticizer than adipic acid and the extra methyl group can result in higher hydrophobicity in the target polymer utilizing the plasticizer. Furthermore, the olefinic bonds (carbon-carbon double bonds) in unsaturated dicarboxylic acids, e.g. muconic acid, can be modified to introduce other advantages in the final targeted polymer (e.g. further permeability reduction, flame resistance groups, etc.). Note that as used herein, the term "muconate" can be used to refer to the esters or salts of the muconic acids (in which muconic acid is the free-acid/protonated molecule 2,4-hexadienedioic acid (2,4-HAD)). Another aspect of the present disclosure is the synthesis of saturated and unsaturated DCAs from alkylated phenol compounds, which may then be used to produce the novel monomers and polymers described herein.

In general, the present disclosure relates to reacting the double bonds present in unsaturated dicarboxylic acids (DCAs), e.g. with thiol-containing molecules, to functionalize the DCAs, before the DCAs are reacted with other molecules (e.g. a diamine) to make larger molecular weight products (e.g. polymers). Or, in some embodiments of the present disclosure, the DCA may be first reacted with other molecules (e.g. a diamine) to make larger molecular weight products (e.g. polymers) such that the DCA double bonds are present in the larger molecule, so that they may be subsequently reacted with other molecules (e.g. thiol-containing molecules) to further modify the larger molecular weight products.

Structure 1 and Structure 2 illustrate exemplary structures of DCAs, muconic acid (i.e. 2,4-HAD) and a methylated muconic acid, 2-methyl-2,4-hexadienedioic acid, respectively, which may be used to produce novel polymers and/or plasticizers as described below.

Structure 1

Structure 2

Structures 1 and 2 can be represented by the generalized structure below (Structure 3):

Structure 3

For the case of a simple straight chain positioned between two carboxylic acid groups, e.g. muconic acid (Structure 1), R includes at least one carbon-carbon double bond. The straight-chained (unbranched) muconic acid is an example of a C6 dicarboxylic acid for which R is equal to four carbon atoms, including two carbon-carbon double bonds in the chain. Other examples (other than muconic acid) of unbranched, straight-chained, bioderived dicarboxylic acids, containing at least one olefinic bond, are shown below in Scheme 1. This list is provided for illustrative purposes and is not limiting. For example, longer chained DCAs containing one or more olefinic bonds are considered within the scope of the present disclosure.

Scheme 1: Straight-Chained Unsaturated Dicarboxylic Acids

Thus, referring again to Structure 3, in some embodiments of the present disclosure, R may be an unbranched carbon chain having between 2 and 5 carbon atoms inclusively, containing one or two carbon-carbon double bonds.

For the case of a branched straight chain positioned between two carboxylic acid groups e.g. 2-methyl-2,4-hexa-dienedioic acid (Structure 2), in addition to the at least one carbon-carbon double bond, R may also include at least one alkyl group; e.g. a methyl group, an ethyl group, a propyl group, a butyl group, etc. The methylated muconic acid of Structure 2 is an example, now referring to Structure 3, of a C6 dicarboxylic acid for which R is equal to four carbon atoms, including two carbon-carbon double bonds and a methyl group. Thus, in some embodiments of the present disclosure, R may be between 2 and 5 carbon atoms, inclusively, and may contain one or two carbon-carbon double bonds, where $R_1$ (see below) is an alkyl group, either straight-chained or branched, with between 1 and 10 carbon atoms. Examples of branched, olefinic DCAs, within the scope of the present disclosure, include those shown in Scheme 2 below. This list is provided for illustrative purposes and is not limiting. For example, longer chained DCAs containing branched hydrocarbon chains having one or more olefinic bonds are considered within the scope of the present disclosure. Also, although not shown in Scheme 2, in some embodiments of the present disclosure, a branched, olefinic DCA may contain more than when alkyl group.

Scheme 2: Branched Unsaturated Dicarboxylic Acids

Thus, from Schemes 1 and 2, and referring to generalized Structure 3, R may include between 2 and 5 carbon atoms, positioned between the two carboxyl end groups, and R may or may not have a functional group attached to it, as represented by $R_1$ in Scheme 2. In some embodiments of the present disclosure, $R_1$ may be an aromatic and/or a simple hydrocarbon and/or it may contain other elements including for example, oxygen, nitrogen, phosphorous, and/or sulfur. So, $R_1$ may be constructed of elements other than carbon and hydrogen. Referring to the list of examples above, specific examples of $R_1$ according to some embodiments of the present disclosure include a methyl group, but may also include a heteroatom-containing groups such as chlorine or fluorine, and/or a carboxylic acid.

As stated above, the double bonds of an unsaturated DCA provide useful reaction sites that may be utilized to make unique intermediates and/or products. For example, unsaturated 2,4-HDA (Structure 1) may be reacted with a sulfur-containing reactant such as butanethiol or thiophenol to produce compounds like that shown in Structure 4 and Structure 5:

Structure 4

Structure 5

Thus, $R_2$ may include an aromatic and/or an alkyl group, a simple hydrocarbon, and/or $R_2$ may contain other elements including for example, oxygen, nitrogen, phosphorous, and/or sulfur. Referring to Structure 4, specific examples of $R_2$, according to some embodiments of the present disclosure, include at least one of a methyl group, an ethyl group, an aromatic group, a phosphate group and/or a butyl group. Thus, in general, the carbon-carbon double bonds contained in R of generalized Structure 3 may be reacted with a thiol group to produce generalized Structure 6, Structure 6 where $R_3$ may be a straight or branched, unsaturated or partially unsaturated, chain having at least one sulfur-containing functional group. According to some embodiments of the present disclosure, specific examples where $R_3$ is a sulfur-functionalized straight chain positioned between the two carboxylic acid groups are summarized in Scheme 3 below, where $R_4$ may be, for example, an aromatic functional group, for example a benzene ring, an alkyl side chain, a dithiol (to cross link multiple chains), a carboxylic acid, a hydroxyl, an alkyl side chain containing halogens (e.g. chlorine, fluorine, etc.) and/or other heteroatoms and their respective oxides (e.g. phosphorous or phosphorus oxides). The molecules shown in Scheme 3 are shown for illustrative purposes and are not limiting.

Scheme 3: Straight-Chained Functionalized Dicarboxylic Acids

-continued

According to some embodiments of the present disclosure, referring again to Structure 6, examples where $R_3$ is a sulfur-functionalized branched chain positioned between two carboxylic acid groups are summarized in Scheme 4 below. For example, $R_4$ may be an aromatic functional group, for example a benzene ring an alkyl side chain, a dithiol (to cross link multiple chains), a carboxylic acid, a hydroxyl, an alkyl side chain containing halogens (e.g. chlorine, fluorine, etc.) or other heteroatoms and their respective oxides (e.g. phosphorous or phosphorus oxides). The molecules shown in Scheme 4 are shown for illustrative purposes and are not limiting.

Scheme 4: Branched Functionalized Dicarboxylic Acids

In some embodiments of the present disclosure, an unsaturated DCA, e.g. 2,4-HDA, may be reacted by Diels-Alder Reactions to produce a molecule like that shown for Structure 7:

Structure 7 where Structure 7 may be reacted as described below, like the other DCAs described herein, to produce novel polymers and or plasticizers.

In addition, in some embodiments of the present disclosure, the carbon-carbon double bonds (as shown in Schemes 1 and 2) may be converted to saturated bonds by hydrogenation. For the example of 2,4-HDA, the 2,4-HDA may be hydrogenated to produce hexanedioic acid. Thus, in some embodiments of the present disclosure, any of the structures represented by Structure 3 and illustrated in Schemes 1 and 2 may be saturated (i.e. any carbon-carbon double bonds have been hydrogenated) or partially saturated/unsaturated (e.g. functionalized with a sulfur-containing groups, while still containing at least one carbon-carbon double bond).

Structures 4-6 and Schemes 3 and 4 provide examples of products made by reacting the carbon-carbon double bonds of saturated DCAs (e.g. 2,4-HDA) before the DCA frame- work is incorporated into larger molecular weight molecules (e.g. polymers). However, in some embodiments of the present disclosure, a saturated DCA may first be reacted with another molecule to produce a larger molecule (e.g. dimer, oligomer, and/or polymer) such that the carbon-carbon double bond(s) are maintained in the larger molecule to be reacted in a subsequent reaction or reactions. Reaction 1 shows the reaction of 2,4-HDA with a diamine to form a homopolymer, where the carbon-carbon double bonds of the 2,4-HDA repeat unit is subsequently reacted as shown in Reaction 2 with a sulfur-functionalized benzene ring to produce a benzene-functionalized homopolymer and/or copolymer. As defined herein, the product of Reaction 2 is referred to herein as a "homopolymer" when all of the olefinic bonds react to form benzene functional groups, whereas a polymer containing both unreacted olefinic bonds and some benzene functional groups, in different monomer subunits, is referred to herein as a "copolymer". Referring to these reactions, n may be between 2 and 1000, inclusively.

Reaction 1

Reaction 2

Although Reactions 1 and 2 show the specific reactions of muconic acid with 1,6-hexanediamine, any of the olefinic DCAs described by Structure 3 and illustrated in Schemes 1 and 2 may be reacted with a diamine to produce a product similar in structure and functionality to that shown in Reaction 1. The general reaction for reacting an olefinic DCA with a diamine is represented by Reaction 3, Reaction 3 where the DCA corresponds to the general structure of a DCA (Structure 3) and the diamine may be any diamine where $R_5$ is a hydrocarbon chain. In some embodiments of the present disclosure, $R_5$ may be a saturated hydrocarbon chain having between 1 and 10 carbon atoms. In some embodiments of the present disclosure, $R_5$ may be a branched hydrocarbon chain having one or more of an alkyl group and/or a functional group that include one or more elements other than, or in addition to, carbon and hydrogen. Specific non-limiting examples of diamines suitable for Reaction 3 include straight-chained hydrocarbons end-capped with two amine groups where the chain is a saturated hydrocarbon chain having between 1 and 10 carbon atoms. The generalized product of Reaction 3, the olefinic bonds in particular, may then be reacted with a reactant having a thiol group as shown below in generalized Reaction 4, Reaction 4 where $R_3$ is as defined above for Structure 6 and x corresponds to the number of olefinic bonds contained in R.

Figure 1:
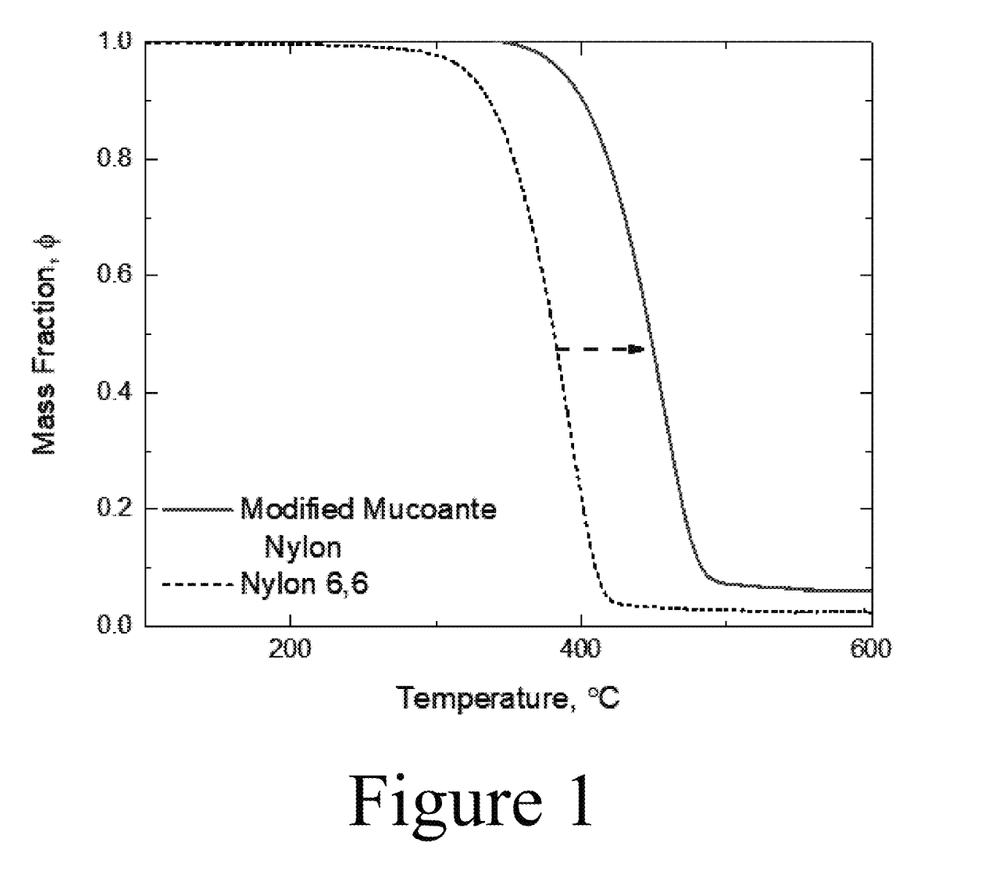
FIG. 1 illustrates the temperature dependent degradation of homopolymers and/or copolymers containing modified bioderived dicarboxylic acid repeat units, according to some embodiments of the present disclosure.

The product of Reaction 2, as shown herein, has improved temperature resistance and/or flame resistance. In some embodiments of the present disclosure, Reaction 2 was completed by dissolving the olefinic polymer resulting from Reaction 1 in N-methyl-2-pyrrolidone (NMP) and stirring overnight with thiobenzene. FIG. 1 illustrates the thermal gravimetric analysis of nylon-6,6 compared to a modified nylon having the structure of the product shown in Reaction 2 above. The modified nylon based on 2,4-HDA exhibits improved temperature stability over the nylon-6,6.

Figure 2:
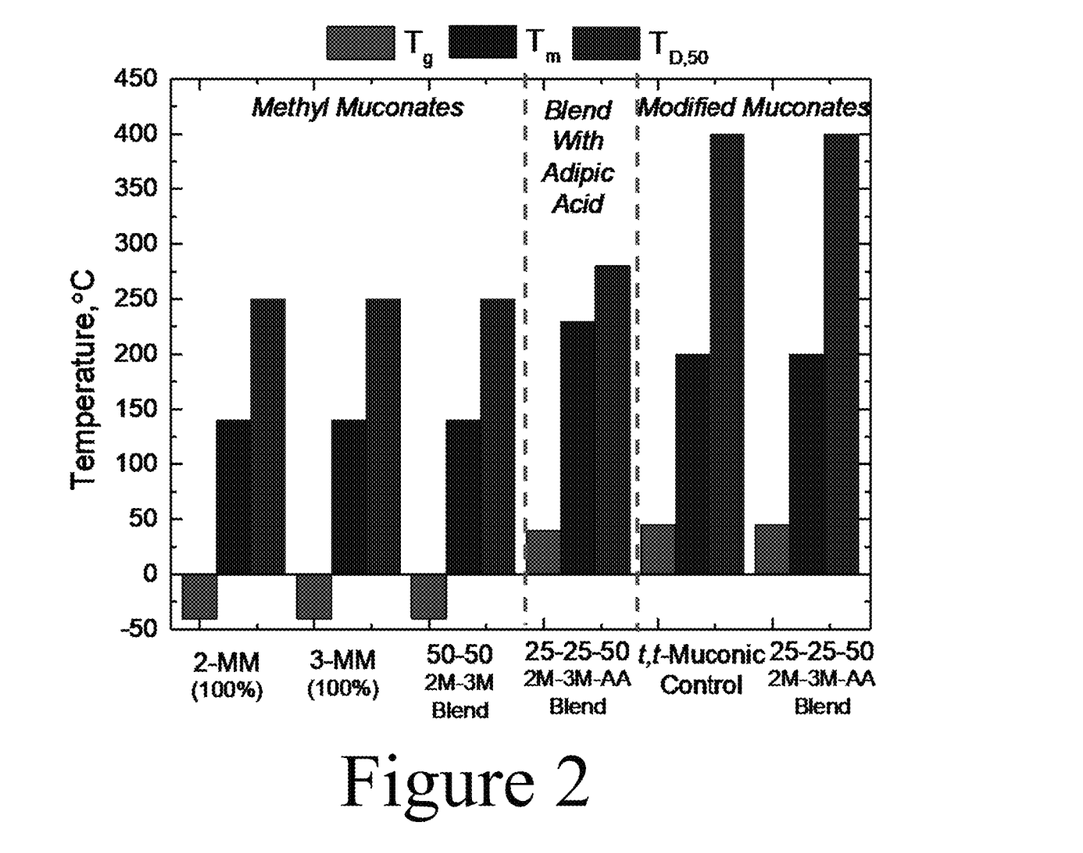
FIG. 2 illustrates the physical properties of polymers made from bioderived dicarboxylic acids, according to some embodiments of the present disclosure.

FIG. 2 compares the glass transition temperatures ($T_g$), melting points ($T_m$), and decomposition temperatures ($T_{D, 50}$) for nylons synthesized from the equimolar reaction of hexamethyl diamine (HMDA) with carboxylic acids (columns 1-4) to form nylons and two respective nylons modified post polymerization. Specifically, data is provided for the nylons in which the carboxylic acids are: 2-methyl muconate (2-methyl-2,4-hexadienedioic acid), 3-methyl muconate (3-methyl-2,4-hexadienedioic acid), a blend 50-50 of 2-methyl muconate and 3-methyl muconate

[2-methyl-2,4-hexadienedioic acid and 3-methyl-2,4-hexadienedioic acid], and a 25%, 25%, 50% blend of 2-methyl muconate, 3-methyl muconate [2-methyl-2,4-hexadienedioic acid and 3-methyl-2,4-hexadienedioic acid], and adipic acid. The left two columns refer to a trans-trans muconate control modified with benzenethiol (Reaction 2) and a 25-25-50 blend. FIG. 2 illustrates that the modified methyl muconates possess nylon properties when copolymerized with adipic acid and can be modified to outperform the other nylons with respect to thermal decomposition temperatures, while maintaining the other requisite thermal properties. Further thermal properties of select nylons are reported in Table 2.

TABLE 2

Performance Advantages of Nylons made using Alkylated DCAs

| Adipic | 2-methyl muconate | 3-methyl muconate | $T_g$ | $T_m$ |
|---|---|---|---|---|
| 100 | — | — | 60 | 260 |
| — | 100 | — | −40 | 140 |
| — | — | 100 | −40 | 140 |
| — | 50 | 50 | −40 | 140 |
| 50 | 25 | 25 | 40 | 230 |

Structure 8

Structure 8 illustrates an exemplary structure for an adipate-co-2-methyl muconate-co-2-methyl muconate copolymer made using the ratios shown in Table 2. The sum of m, n, and o can range from 2 to 1,000 and in the last line of Table 2 m=2n=2o. The homopolymers of the methyl muconates with hexamethyldiamine resulted in a polymer that has lower thermal properties when compared to nylon-6,6. Additionally, copolymers of the 2-methyl and 3-methyl muconates do not exhibit any different performance, enabling the use of mixed 2-methyl muconate and 3-methyl muconate streams to produce unique copolymers. When copolymers of methyl muconates and adipic acid were made, an ideal nylon was synthesized with methyl groups added to enable other performance enhancements (e.g. lower water permeabilities).

Although Reaction 1-4 illustrate condensation reactions between amine groups and carboxylic acids to make intermediate polymers containing olefinic groups (Reactions 1 and 3), followed by reacting the olefinic groups with a thiol-functionalized reactant to make the final products (Reactions 2 and 4), in some embodiments, the order may be reversed. For example, in a first reaction, the olefinic groups of muconic acid may first be reacted with a thiol-functionalized reactant. This may then be followed by a second reaction between the carboxylic acid groups of the now functionalized molecule with a diamine to produce the homopolymer and/or copolymer products shown in Reactions 2 and 4.

Further, according to some embodiments of the present disclosure, the carboxyl groups of unsaturated DCAs and/or saturated DCAs may be condensed with alcohols to produce unique compounds, diesters, suitable for use as plasticizers in plastic compositions/blends. Examples of both, unsaturated and saturated diesters are shown below in Structure 8 and Structure 9.

Structure 8

Structure 9

$R^1$ and $R^2$ may be the same or different. Thus, $R^1$ and/or $R^2$ may include an aromatic and/or an alkyl group, a simple hydrocarbon, and/or R may contain other elements including for example, oxygen, nitrogen, phosphorous, and/or sulfur. Therefore, any of the dicarboxylic acids represented by Structure 3 and illustrated in Schemes 1 and 2, and their saturated equivalents, may be reacted with an alcohol (esterification) to form a diester, which as shown below, may have properties very well suited as plasticizers. A generalized reaction for reacting a DCA with an alcohol to produce a diester is shown below in Reaction 5. Again, $R_1$ and $R_2$ in Reaction 5 may be derived from the same alcohol or a different alcohol.

Reaction 5

Structure 10 and Structure 11 illustrate specific examples of such diester plasticizers, such as di(2-ethylhexyl phthalate) (DEHP) and di(2-ethyl-hexyl) adipate according to some embodiments of the present disclosure, where saturated muconic acid and 2-methyl-2,4-hexadienedioic acid were esterified with 2-ethyl hexanol.

Structure 10

Structure 11

Figure 3:
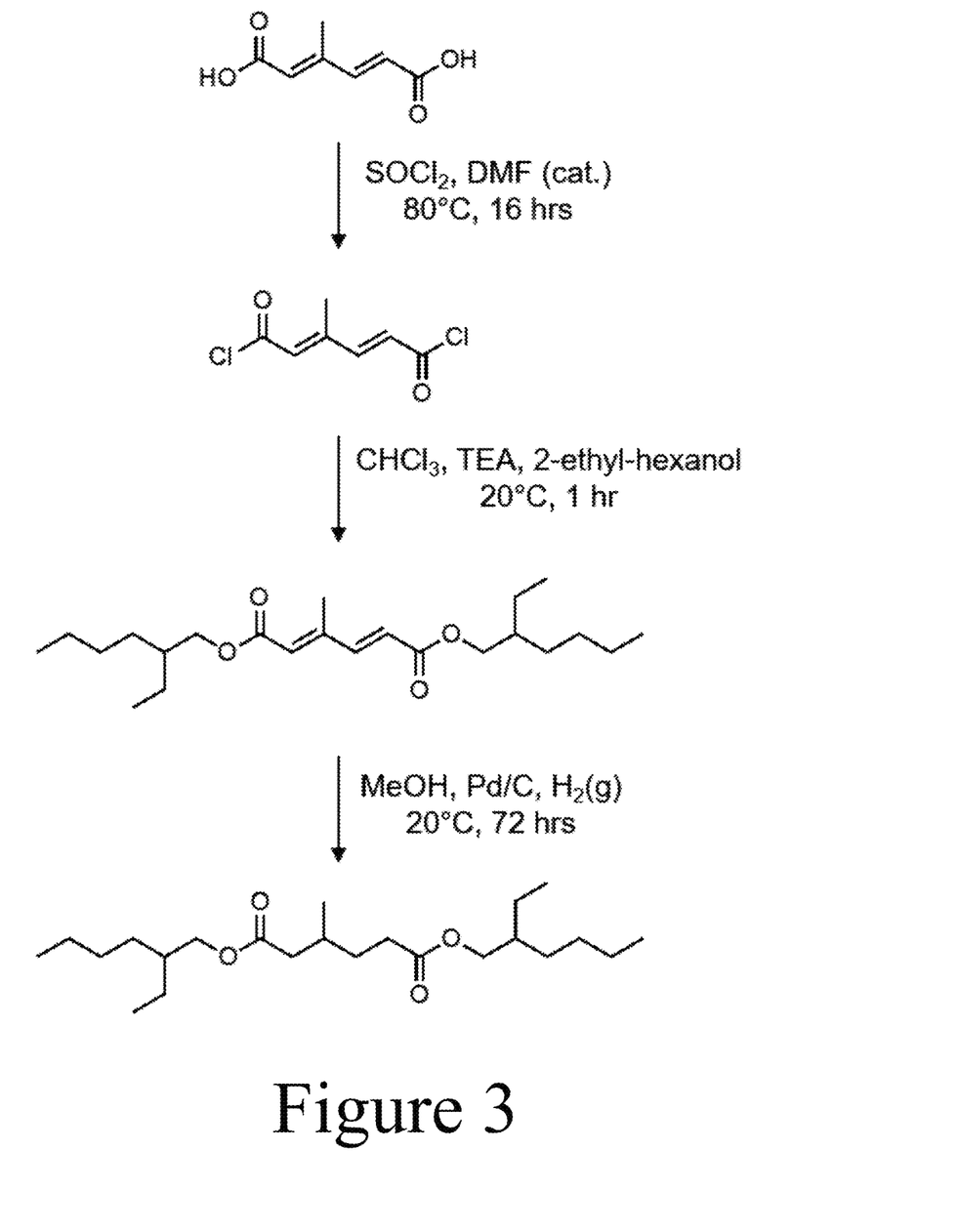
FIGS. 3 and 4 illustrate reaction routes to bioderived, dicarboxylic-based materials that may be used as plasticizers, according to some embodiments of the present disclosure.

FIG. 3 illustrates one embodiment of a reaction route to product plasticizers based on 3-methyl-2,4-hexadienedioic acid Initially, the dicarboxylic acid is converted to an acyl chloride for facile reactivity and subsequently reacted with 2-ethyl hexanol to produce the methyl-muconate plasticizers. Subsequently, the methyl muconate plasticizer can be hydrogenated to make methyl adipate plasticizers.

Figure 4:
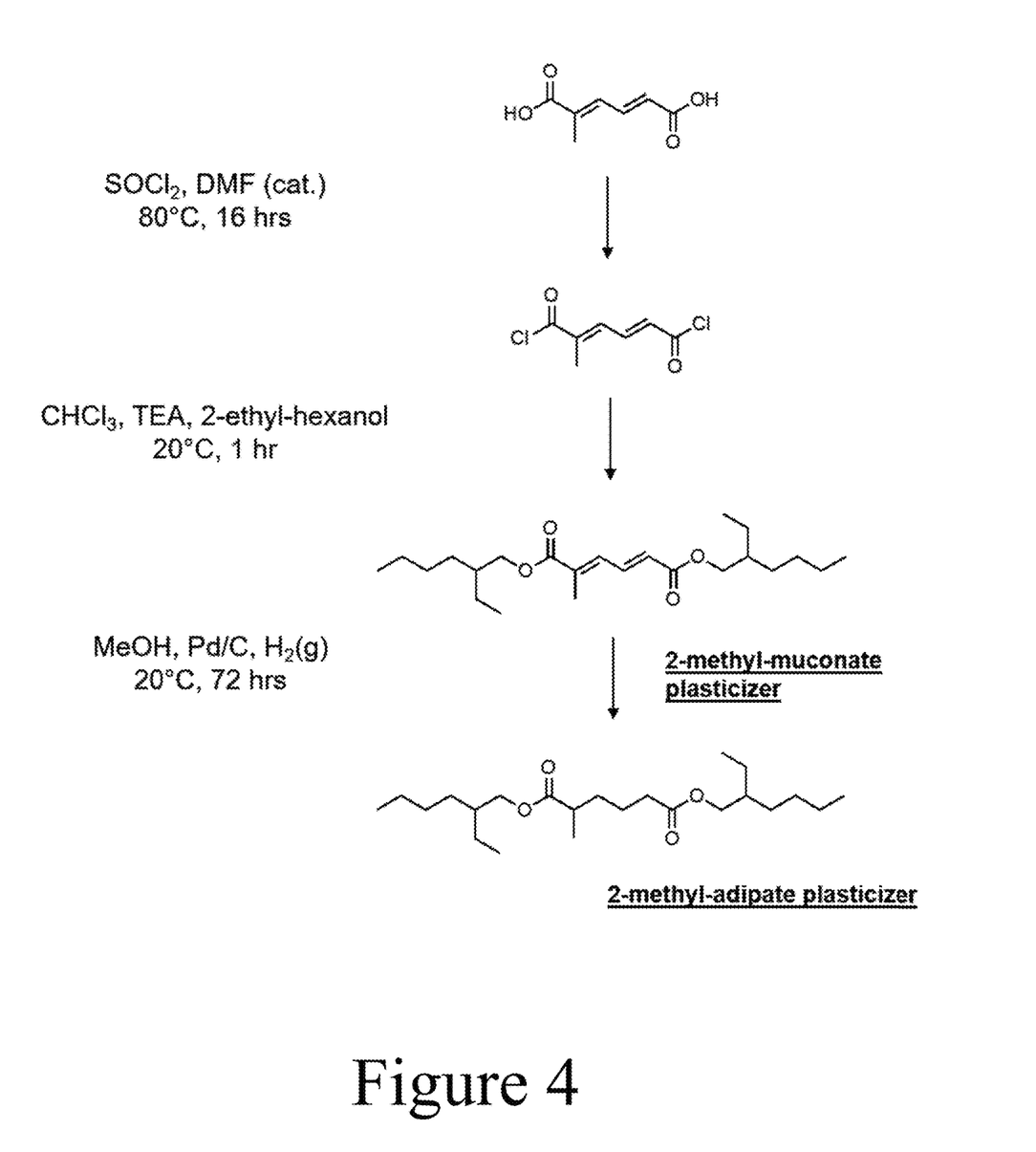

FIG. 4 illustrates one embodiment of a reaction route to product plasticizers based on 2-methyl-2,4-hexadienedioic acid. Initially, the dicarboxylic acid is converted to an acyl chloride for facile reactivity and subsequently reacted with 2-ethyl hexanol to produce the methyl-muconate plasticizers. Subsequently, the methyl muconate plasticizer can be hydrogenated to make methyl adipate plasticizers.

Table 1 illustrates a comparison of a polyvinyl chloride (PVC) plastic using either adipic acid as a plasticizer or a methylated DCA as a plasticizer, where each plasticizer was blended with the PVC. Table 1 illustrates that reductions in the glass transition temperature ($T_g$) may be obtained using alkyl-functionalized DHAs and/or their hydrogenated, saturated forms.

TABLE 1

| $T_g$ of PVC as a function of plasticizer loading | | |
|---|---|---|
| Diacid | Loading (wt. %) | $T_g$ |
| Adipic | 1 | 90 |
|  | 5 | 74 |
| Methyl-Muconate | 1 | 89 |
|  | 5 | 67 |

Figure 5:
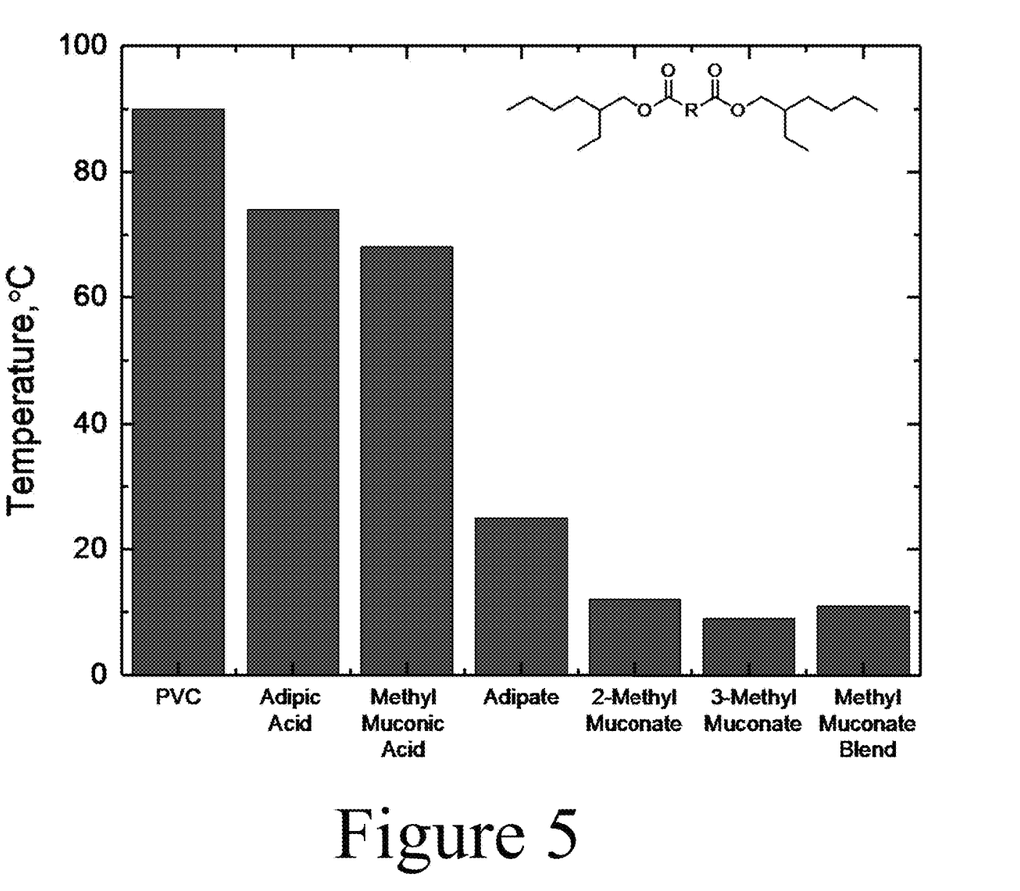
FIG. 5 illustrates a comparison of the plasticizing potential of various materials, including plasticizers derived from bioderived dicarboxylic acids, according to some embodiments of the present disclosure.

FIG. 5 illustrates the glass transition temperature for PVC (virgin PVC in the far left column) and PVC plasticized with 10 wt. % adipic acid, methyl muconic acid, and the 2-ethylhexyl diesters of adipic acid, 2-methyl muconic acid, 3-methyl muconic acid, and a 50-50% blend of the methyl muconic esters. The blend of 2 and 3 methyl muconic behaves the same as the pure methyl-muconate compounds, and the methyl-muconates are twice as effective at plasticization as the adipic analogue.

An aspect of the present disclosure is the synthesis of saturated and unsaturated DCAs from alkylated phenol compounds. For example, 3-methyl-phenol may be converted to 3-methyl-1,2-benzenediol, which may then be converted to 2-methyl-2-4-hexadienedioic acid (see Structure 2 above). Another example is the conversion of 4-methyl-phenol to 4-methyl-1,2-benzenediol, which may be subsequently converted to 3-methyl-2,4-hexadienedioic acid, Structure 11.

Structure 11

Once made, and as described above, the saturated and/or unsaturated DCAs may be utilized to produce an array of various molecules, including functionalized monomers, plasticizers, and/or polymers, with examples of possible polymers including nylons, and/or polyesters (saturated and unsaturated).

Whether or not a reactant or product described herein is "bioderived" may be determined by analytical methods. Using radiocarbon and isotope ratio mass spectrometry analysis, the bio-based content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pNMC value obtained correlates directly to the amount of biomass material present in the sample. Thus, ASTM-D866 may be used to validate that the compositions described herein are and/or are not derived from renewable sources.

EXAMPLES

Example 1

A composition comprising: a first repeat unit defined by wherein: R comprises a first hydrocarbon chain comprising at least one olefinic bond, $R_5$ comprises a second hydrocarbon chain, the second hydrocarbon chain is saturated, and n is between 2 and 1,000.

Example 2

The composition of Example 1, wherein the first hydrocarbon chain comprises between 3 and 10 carbon atoms.

Example 3

The composition of Example 2, wherein the first hydrocarbon chain further comprises at least one alkyl group.

Example 4

The composition of Example 3, wherein the alkyl group comprises at least one of a methyl group, an ethyl group, a propyl group, or a butyl group.

Example 5

The composition of Example 1, wherein the second hydrocarbon chain comprises between 3 and 10 carbon atoms.

Example 6

The composition of Example 1, wherein R comprises at least one of comprises an alkyl group.

Example 7

The composition of Example 6, wherein the alkyl group comprises at least one of a methyl group, an ethyl group, a propyl group, or a butyl group.

Example 8

The composition of Example 1, further comprising: a second repeat unit defined by, wherein: R* comprises a third hydrocarbon chain that may be saturated or unsaturated, $R_5$* comprises a fourth hydrocarbon chain, the fourth hydrocarbon chain is saturated, and m is between 2 and 1,000.

Example 9

The composition of Example 8, further comprising: a third repeat unit defined by, wherein: R comprises a fifth hydrocarbon chain that may be saturated or unsaturated, $R_5$ comprises a sixth hydrocarbon chain, the sixth hydrocarbon chain is saturated, and o is between 2 and 1,000.

Example 10

The composition of Example 9, comprising:

Example 11

A composition comprising: a first repeat unit defined by wherein: $R_3$ comprises a first hydrocarbon chain comprising at least one sulfur containing functional group, $R_5$ comprises a second hydrocarbon chain, the second hydrocarbon chain is saturated, and n is between 2 and 1,000.

Example 12

The composition of Example 11, wherein the first hydrocarbon chain comprises between 3 and 10 carbon atoms.

Example 13

The composition of Example 12, wherein the first hydrocarbon chain further comprises at least one alkyl group.

Example 14

The composition of Example 13, wherein the alkyl group comprises at least one of a methyl group, an ethyl group, a propyl group, or a butyl group.

Example 15

The composition of Example 12, wherein the second hydrocarbon chain comprises between 3 and 10 carbon atoms.

Example 16

The composition of Example 12, wherein $R_3$ comprises at least one of

-continued

-continued $R_1$ comprises an alkyl group, and $R_4$ comprises at least one of an aromatic group, an alkyl group, a dithiol group, a carboxylic acid, a hydroxyl group, or a halogen.

Example 17

The composition of Example 11 comprising:

Example 18

The composition of Example 11, further comprising: a second repeat unit defined by wherein: $R_3{}^*$ comprises a third hydrocarbon chain may or may not comprise at least one sulfur containing functional group, $R_5{}^*$ comprises a fourth hydrocarbon chain, the fourth hydrocarbon chain is saturated, and m is between 2 and 1,000.

Example 19

The composition of Example 18, further comprising: a third repeat unit defined by wherein: $R_3{}^{}$ comprises a fifth hydrocarbon chain may or may not comprise at least one sulfur containing functional group, $R_5{}^{}$ comprises a sixth hydrocarbon chain, the sixth hydrocarbon chain is saturated, and o is between 2 and 1,000.

Example 20

A composition comprising wherein: R comprises a first hydrocarbon chain, $R^1$ comprises a second hydrocarbon chain, and $R^2$ comprises a third hydrocarbon chain.

Example 21

The composition of Example 20, wherein at least one of R, $R^1$, or $R^2$ is saturated.

Example 22

The composition of Example 20, wherein at least one of R, $R^1$, or $R^2$ is unsaturated.

Example 23

The composition of Example 20, wherein at least one of R, $R^1$, or $R^2$ is a straight chain having between 3 and 10 carbon atoms.

Example 24

The composition of Example 23, wherein the straight chain further comprises at least one alkyl group.

Example 25

The composition of Example 24, wherein the alkyl group comprises at least one of a methyl group, an ethyl group, a propyl group, or a butyl group.

Example 26

The composition of Example 20 having the structure

Example 27

The composition of Example 20 having the structure

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:

wherein:

m is between 2 and 1,000, n is between 2 and 1,000, and o is between 2 and 1,000.

2. A composition comprising:

wherein n is between 2 and 1,000.

3. A composition comprising:

* * * * *